(12) United States Patent
Bashiri et al.

(10) Patent No.: US 6,616,676 B2
(45) Date of Patent: Sep. 9, 2003

(54) DEVICES AND METHODS FOR REMOVING OCCLUSIONS IN VESSELS

(75) Inventors: Mehran Bashiri, San Carlos, CA (US); Alain Cornil, Mountain View, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/832,444

(22) Filed: Apr. 10, 2001

(65) Prior Publication Data

US 2002/0147459 A1 Oct. 10, 2002

(51) Int. Cl.⁷ .............................................. A61B 17/22
(52) U.S. Cl. ........................................................ 606/159
(58) Field of Search .................. 606/159, 170, 606/167

(56) References Cited

U.S. PATENT DOCUMENTS

| | | |
|---|---|---|
| 3,367,101 A | 2/1968 | Garner et al. |
| 3,435,826 A | 4/1969 | Fogarty |
| 4,030,503 A | 6/1977 | Clark, III |
| 4,403,612 A | 9/1983 | Fogarty |
| 4,890,611 A | 1/1990 | Monfort et al. |
| 4,923,642 A | 5/1990 | Rutzen et al. |
| 4,990,134 A | 2/1991 | Auth |
| 5,078,722 A | 1/1992 | Stevens |
| 5,314,438 A | 5/1994 | Shturman |
| 5,411,509 A | 5/1995 | Hilal |
| 5,423,804 A * | 6/1995 | Kulick ......................... 606/14 |
| 5,423,838 A | 6/1995 | Willard |
| 5,490,859 A | 2/1996 | Mische et al. |
| 5,674,235 A * | 10/1997 | Parisi ........................... 604/22 |
| 5,836,957 A | 11/1998 | Schulz et al. |
| 5,947,985 A * | 9/1999 | Imran .......................... 606/159 |
| 6,001,112 A | 12/1999 | Taylor |
| 6,080,170 A * | 6/2000 | Nash et al. .................. 606/159 |
| 6,135,991 A * | 10/2000 | Muni et al. .................... 604/22 |
| 6,152,919 A | 11/2000 | Hakky |
| 6,152,938 A * | 11/2000 | Curry .......................... 606/159 |
| 6,156,048 A * | 12/2000 | Wulfman et al. ........... 606/159 |

* cited by examiner

*Primary Examiner*—Ismael Izaguirre
(74) *Attorney, Agent, or Firm*—Robins & Pasternak LLP

(57) ABSTRACT

Occlusion-removing devices that include an inflatable balloon for arresting blood flow and a occlusion-shearing element are provided. Also provided are methods of making and using these devices.

19 Claims, 1 Drawing Sheet

DEVICES AND METHODS FOR REMOVING OCCLUSIONS IN VESSELS

FIELD OF THE INVENTION

This invention relates to devices and methods for removing an occlusion from a vessel.

BACKGROUND

This surgical device is designed to remove occlusions found in the human vasculature and thereby increase blood flow to and around the occluded site.

Emboli occasionally form around the valves of the heart and then are dislodged and follow the blood flow into the distal regions of the body. They are particularly dangerous if the emboli is transmitted to the brain where it results in an embolic stroke. As will be discussed below, many such occlusions occur in the middle cerebral artery (MCA), although such is not the only site where emboli come to rest. When blood flow is inhibited or cut off completely from a portion of the brain, the brain's oxygen supply is limited causing severe problems.

Such vaso-occlusions occur in a wide variety of sites within the body. The lodging of thrombus in various sites is complicated by the presence of atherosclerosis. This disease causes the vessels to become tortuous and narrowed. These anomalies are often considered to be the result of the growth of atherosclerotic plaque. Clots occurring in these diseased vessels are difficult to remove using known catheters.

The use of inflatable balloons to remove emboli has been practiced for many years. The "Fogarty catheter" has been used, typically in the periphery, to remove clots from arteries found in legs and in arms. These well known devices have been described in some detail in U.S. Pat. No. 3,435,826, to Fogarty. Other balloon-type devices are described, for example, in U.S. Pat. Nos. 4,403,612; 3,367,101; 5,078,722; 5,836,957; and 6,152,909.

Another approach for removing embolisms involves the use of an abrading device carried at the distal end of a flexible drive shaft. Examples of such devices are described, for example, in U.S. Pat. No. 4,990,134 (Auth) and U.S. Pat. No. 5,314,438 (Shturman) which describe the use of abrasive material such as diamond grit (diamond particles or dust) to remove hardened, calcified atherosclerotic plaques. Emboli fragmenting devices have also been described, for example, in U.S. Pat. No. 5,423,838. Other patents describe the use of cutting blades, typically extendable from a housing assembly for removing the occlusion by fragmentation. See, for example, U.S. Pat. Nos. 4,030,503; 4,890,611; 5,411,509; 5,490,859; 6,001,112; 5,423,838; and 4,923,462. These devices typically contain a catheter shaft, a drive shaft for spinning the material movement element within the blood vessel, and a collection portion placed on the material removal element for collecting any occlusion material removed by the expandable material removal element. The drive shaft may be operated by a motor connected to the drive shaft proximate to the proximal end of the drive shaft.

Despite the advances made using these devices, removal of emboli using either balloon catheters or mechanical fragmenting devices is rife with potential problems. When attempting to remove a clot using a balloon catheter, the resistance to such removal often causes the balloon portion of the catheter to evert over the tip of the catheter. Should the user need to partially deflate the balloon during such a deflation, the distal tip of the balloon may become distended and angulate. Another difficulty with balloon catheters is the possibility of damage to the intima of arteries. Inflation pressures can create forces significant enough to share such a vessel lining or dislodge plaque lodged on such a wall. In the worst case, the balloon may rupture leaving balloon portions in the bloodstream. Movement of a balloon can displace the clot through more proximal branches into other large vessels such as the internal carotid artery (ICA) and then into other vessels. Furthermore, if the occlusion is a blood clot or soft tissue thrombus, such as those that may occur in the peripheral vasculature, for instance, the soft tissues of the thrombus may sufficiently resist the molding action of the dilating member (i.e. may be too elastic) to prevent conventional angioplasty from permanently restoring vascular blood flow. In addition, even if the occlusion is successfully molded, thereby revascularizing the vessel and restoring blood flow therethrough, there is a chance that the occlusion may recur because the occluding material is not removed from the vascular lumen, thereby necessitating repeated or alternative treatments.

Mechanical fragmenting devices can also cause serious problems during clot removal. For example, because embolisms are often asymmetrical or are similar in mechanical properties to the surrounding tissue, many of these devices can damage healthy tissue while removing the clot. Furthermore, many fragmenting devices are not suited to removing both hard and soft occlusions. Additionally, the fragments generated by mechanical fragmentation cannot always be efficiently removed and can cause problems if they are carried by the blood to remote locations.

Thus, notwithstanding the foregoing and other efforts to design a embolic removal devices, there remains a need for such a device which can efficiently remove all sorts of emboli while providing minimal risk to the surrounding vessel wall. None of the currently available devices approximates the design of the device described below.

SUMMARY OF THE INVENTION

In one aspect, the invention includes a device for removing occlusions from a vessel, comprising (a) a housing element having a distal end, a proximal end and a longitudinal axis, wherein one or more lumens are disposed along the longitudinal axis; (b) an embolism collector element (e.g., a vacuum aspirator); (c) a cutting element attached to the distal end of the drive shaft; and (c) an inflatable balloon. In certain embodiments, the device further includes one or more of the following components: a fluid channel, a casing (e.g., a cage-like structure) disposed around the cutting element; a drive shaft disposed along the longitudinal axis of the housing and/or a power source (e.g., a micro electro mechanical system (MEMS) motor). In any of these devices, the cutting element may be smooth, roughened and/or may have perforations therein. Similarly, in any of these devices the housing and/or casing that contacts the cutting element is also surface-modified (e.g., is roughened, perforated, includes braids and/or ribbons, etc.). In embodiments comprising a casing around the cutting element, the casing may extend from the distal end of the housing. In any of the devices described herein, the inflatable balloon is capable of (a) centering the cutting element; (b) at least partially arresting blood flow around the occlusion; or (c) both centering and arresting blood flow.

In another aspect, methods of removing an occlusion in a vessel are provided. The methods comprise accessing a selected site with any of the devices described herein; inflating the balloon to the desired dimensions; shearing at least a portion of the embolism with the cutting element; and removing the sheared fragments of the embolism with the collection element. In certain embodiments, the shearing comprises drawing a portion of the embolism into the housing and manipulating the cutting element to shear the embolism against the interior wall of the housing and/or against the casing, when the casing is present.

These and other embodiments of the subject invention will readily occur to those of skill in the art in light of the disclosure herein.

DESCRIPTION OF THE INVENTION

Figure 1:
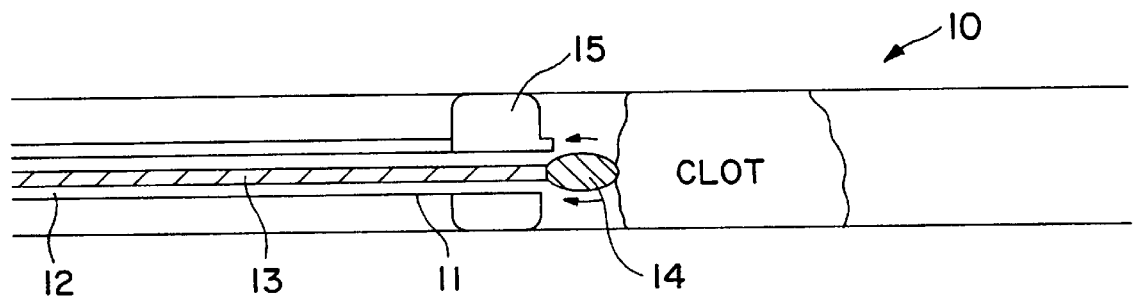
FIG. 1 depicts one embodiments of a clot removal device as described herein.

Devices and methods for the removal of emboli are described. Methods of using these devices also form an aspect of this invention. Currently, mechanical clot removal devices often result in the pieces of the clot being washed away. The present invention solves this and other problems by providing a means to stop blood flow in the vessel that is occluded until the clot is captured, broken up and/or evacuated. The device and methods described herein are particularly effective for the end stages of blood clot removal where the clot has created a large channel to allow blood flow to break up and carry downstream fragments of the clot.

Advantages of the present invention include, but are not limited to, (i) minimizing the potential that fragments of an embolism can be carried to remote locations by blood flow; (ii) providing the operator with the ability to control blood flow around the device; (iii) minimizing the likelihood of vessel perforation; and (iv) providing a device suitable for a wide variety of occlusions.

All publications, patents and patent applications cited herein, whether supra or infra, are hereby incorporated by reference in their entirety.

It must be noted that, as used in this specification and the appended claims, the singular forms "a", "an", and "the" include plural referents unless the content clearly dictates otherwise. Thus, for example, reference to "a cutting element" includes a mixture of two or more such elements and the like.

This device is a surgical implement which is designed to at least partially retrieve emboli situated in human vasculature. It is intended to be used rapidly as a flow restoration device. Even in those instances where the embolism is not or cannot be completely removed, this inventive device is useful in removing a portion of the clot and thereby permitting restoration of partial blood flow. It is suitably flexible to be placed in the distal tortuous vasculature of the brain and hence is useful in treating blocking emboli found there. Accordingly, this device can used as a partial treatment for embolic stroke. As used herein, the terms "embolus," "clot" and "occlusion" are used interchangeably to refer to any blockage (partial or full) of a vessel by any material (e.g., blood, lymph, plaques, etc.)

Thus, in certain aspects, the inventive device combines a cutting element, an inflatable balloon and other elements such that occlusions can be removed. The device disclosed herein is for the recanalization of occluded vascular lumen (e.g., the middle cerebral artery (MCA) lumen), via the steps of accessing the site of the occlusion; expanding an inflatable balloon which is capable of partially or fully arresting blood flow and is also capable of centering the device (particularly the cutting element); mechanically fragmenting at least a portion of the occlusion within the housing or within a protective casing covering the cutting element; and collecting the fragments through the device via a collection element such as a vacuum aspirator.

FIG. 1 depicts selected portions of one variation of the device (10). The assembly typically includes, within a housing (11), for example a catheter body; a collection element (12), for example a vacuum aspirator for removing fragments of the embolus; and a drive shaft (13) operably linked to a cutting element (14) for fragmenting the clot. The housing (11) may include a channel to accommodate a guide wire or may have a fixed wire. Additionally, the housing may be attached to a distal cone to facilitate the delivery of the device over a guide wire.

As shown in FIG. 2, the cutting element can include a fluid channel (20) for introducing and/or removal of fluids. The cutting element can also include multiple channels to incorporate fluid jets for introducing fluids. The cutting element (14) can be external to the assembly housing or can be extendable from the housing. Furthermore, the assembly also includes an inflatable balloon (15) which serves to arrest the flow of blood so that the fragmented pieces of clot are not washed away by the flow of blood. Additionally, the balloon (15) also serves to center the assembly, thereby keeping the cutting element away from the walls of the vessel.

The housing (11), for example a catheter body, may include multiple lumens and/or multiple tubular members positioned within each other. Methods of making and using multi-lumen catheter bodies are well known to those of skill in the art. Any of the lumens or tubular members of the housing can further comprise a removable core or guide wire. Further, portions of the interior surface of one or more the lumens of the housing (11) may be braided (16) or otherwise modified on the inner surface to help shear the embolic material against the cutting element (14). The placement of a braid or other surface modifications can vary along the length of the assembly, but is desirably at least from the distal end of embolism collector element to the proximal end of the cutting element. Braids can be made, for example, of a superelastic alloy, stainless steel, radioopaque materials such as platinum, and even organic and inorganic fibers or ribbons such as KEVLAR and carbon fiber or combinations of the foregoing. A desirable variant is the substitution of one or more ribbons of the braid (or the addition of one or more ribbons) with a radio-opaque material such as platinum. This obviously permits the user to visualize the position of the embolism collector element during the clot removal procedure. Furthermore, surface modifications (such as by roughening the inner surface of the housing) can also enhance shearing. Such surface modifications may be done instead of, or in addition to, other modifications such as braiding.

The housing may further include slots and/or openings dimensioned so that at least a portion of the occlusion can be drawn into the housing through these openings. One or more lumens of the housing are desirably, but not necessarily, made of lubricious material such as polytetrafluoroethylene. Other materials such as polyurethane, polypropylene, polyurethane, polyurethane or polyethyline of polyvinilchloride, and materials widely known and used in this industry can also be used. In certain instances, it may be desirable to etch the outer surface of tubing using known etching techniques to provide a surface suitable for joining for the other layers. Further it is often desirable to use a biocompatible epoxy such as TRA-CON TRA-BOND FDA-2 (Tra-Con, Inc.—Medford, Mass.) as the material which provides adherence between the lumens of the housing.

The devices described herein also include an inflatable balloon, which serves, for example, to arrest the flow of blood and, additionally, to center the cutting element to avoid perforation of the vessel walls. Any suitable inflatable balloon can be used in construction and use of the devices described herein. Preferably, the balloon restricting the blood flow is very short, thereby allowing it to be positioned on curves without straightening the vessel or blocking side branches. As will be apparent to those of skill in the art, the balloon can be manipulated by the operator to restrict blood flow in virtually any amount.

Exemplary cutting elements are shown in FIGS. 2–3. Although not shown in all FIGs, the associated elements such as balloon, optional drive shaft, vacuum channel and the like are all similar in construction to those described above. The cutting element is capable of moving in any direction, including rotating (spinning), longitudinal movement and lateral movement. It will also be apparent that these movements can be imparted to the concurrently or at different times. Lateral and longitudinal movement allow, for example, shearing of the occlusion against the wall of the housing and/or casing, described below. Preferably, the collection element draws at least part of the embolus into the housing (or casing) where the cutting element can be agitated by the operator such that the clot is sheared by the cutting element and adjacent walls of the housing. Thus, to minimize the likelihood of vessel perforation, the cutting element is preferably only slightly extendable from the housing. In other words, the cutting element works in conjunction with the other elements of the device. The collection element is able to draw at least a portion of the clot into the housing, where the cutting element can then be rotated or otherwise manipulated to shear the clot. The fragments are then evacuated by the collection element.

Figures 2A, 2B:
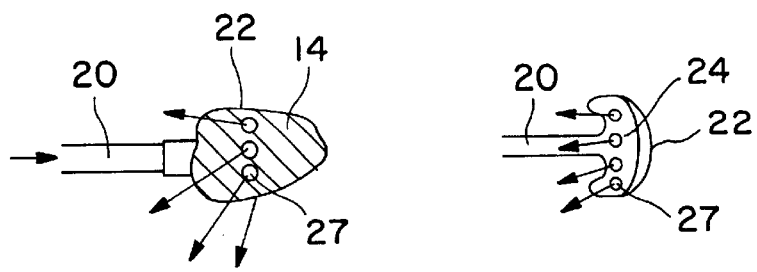
FIGS. 2A and 2B depict variations of the shape and surface modifications of cutting elements useful in the present invention and also depict cutting elements which include a fluid channel disposed therein.

FIGS. 2A and 2B show variations in which the surface (22) of the cutting element is roughened by adding bumps or otherwise modifying the surface. The shape of the metallic burr on the cutting element (24) is also desirably formed such to provide added suction and added vacuum. Any design can be used, shown in FIG. 2A is a cylindrical shape burr, while FIG. 2B depicts a mushroom-shaped burr. Additionally, the cutting element preferably includes perforations (27) through which the clot or fragments thereof can pass through.

Also shown in FIGS. 2A and 2B is fluid channel (20). The channel can be used for distal perfusion, for example with saline (e.g., oxygen enhanced saline). The channel can also be used to introduce any number of pharmaceutically active fluids into the subject including, but not limited to, neuro-protective and/or thrombolytic drugs.

Figure 3A:
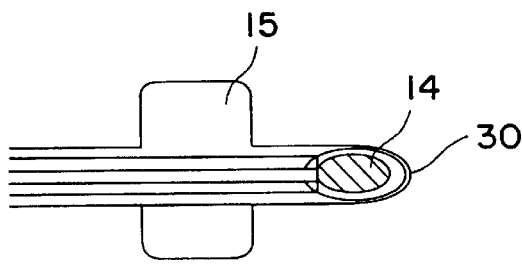
FIGS. 3 and 3B depict other embodiments of a cutting burr, fluid channel and protective casing (e.g., cage) disposed around the cutting element.
Figure 3B:
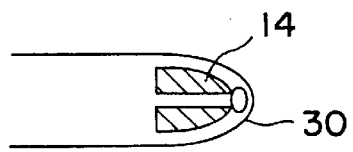

FIGS. 3A and 3B show variations in which the cutting element (14) is placed within a protective casing (30), for example a cage-like structure. As will be apparent the casing is desirably permeable to fluid and/or solid materials of varying dimensions. In embodiments in which the cutting element is within a casing, the cutting element may extend farther from the distal end of the device as perforation of the vessel walls is minimized by the casing. The encased cutting element is preferably still surface roughened such that fragmentation of the clot can be achieved by manipulating the cutter element against the casing.

Like the housing, the casing may further include slots and/or openings dimensioned so that at least a portion of the occlusion can be drawn into the casing and preferably contact the cutting element through these openings. It may be desirable to etch or otherwise roughen the inner and/or outer surface of the casing to facilitate shearing of the occlusion, for example, as described above.

The casing is preferably made of a super-elastic alloy ribbon. Some stainless steels are suitable but the ready availability of nickel-titanium alloys in a wide variety of shapes and sizes makes this choice an easy one. In particular, we have found that ribbons as thin as 0.75 mils in thickness and 2 mils in width are suitable for this device. Thicker and wider ribbons are also suitable in some instances as the situation requires. Preferred ribbons for the embolism collector element are between 0.75 and 1.5 mils in thickness and 3 and 7 mills in width. Most preferred are 0.08 mils and 4 mils respectively. Then use of super-elastic alloys such as nitinol in surgical devices has been previously described (see, e.g., U.S. Pat. No. 6,066,158).

The placement of the embolism collection element (e.g., vacuum) is important only to the extent that it enhance the ability of the overall assembly to collect fragmented portions of the clot. Although FIG. 1 shows the collector element as extending to the distal end of assembly, such is not required. If the collector element proves to be too thick and causes the more distal portion of the element to become inflexible or ungainly, the most distal portion of the element may be omitted. Although the collection element is shown in the FIGs as built-into to the occlusion-removing device, it is to be understood that it can be external to the device and, furthermore, that the collection element could be inserted after the device has been used to shear at least a portion of the occlusion. Vacuum aspirators used in surgical procedures and other suitable collection elements are well known and, in view of the present specification, one of skill in the art could readily include such elements in the devices described herein.

In certain embodiments, the device includes a drive shaft (13) disposed within the housing. Any suitable drive shaft designs can be employed, for example, as described in U.S. Pat. No. 5,423,838. As shown in FIG. 1, the drive shaft occupies the inner lumen of the housing of the assembly. Furthermore, the distal end portion of the shaft (13) is attached to the cutting element. Attachment of the cutting element to the drive shaft may be by any convenient procedure, e.g., soldering, welding, gluing, etc. In embodiments in which the device will carry fluids, the drive shaft is preferably sealed from the rest of the components. Furthermore, as with the housing, the drive shaft can be modified (e.g., by braiding and/or roughening) to enhance shearing of the occlusion within the device.

The operation of the device (e.g., balloon, vacuum and/or cutting element) is preferably controlled by the operator via one or more actuators. For example, the inflatable balloon element is collapsible for passage to the embolism and is expanded as desired at the selected location by the operator. Similarly, the operator can use an actuator to manipulate the cutting element, e.g., using the drive shaft, to shear the occlusion. The embolism collection element and/or fluid channel also preferably are controllable by the operator. As noted above, each element may be operated by a different actuator or, in some embodiments, the same actuator may control more than one element. Furthermore, the actuator may be independently produced from the embolectomy device or may be produced integrally with it. Other procedures and devices may, obviously, be used to expand the balloon.

Thus, one or more functions of the device (e.g., shearing of the occlusion; aspiration, fluid collection and release, etc.) can be achieved using energy supplied by the operator, for instance using an actuator (or actuators) operably linked to the elements of the device that require manipulation. Alternatively, the energy required for one or more of the functions of the device are supplied from a power source, for example, a motor operably linked to the drive shaft or a motor which drives rotation of the cutting element. Power source may supply electrical power, for example alternating current, direct current or alternating current superimposed over the direct current signal. Including links and transmission capability through the catheter and/or device is well within the purview of the skilled artisan, as described for example, in co-owned U.S. Pat. No. 6,168,592. Accordingly, one or more elements of the device may be operably connected to a power source, such as through a power transmission device embedded in, or external to, the device.

In certain embodiments, one or more functions of the device (e.g., rotation of the cutting element) are controlled by a micro-electro-mechanical system (MEMS) or micromotor. An MEMS is a device that transforms mechanical activity into electrical signals and vice versa. (see, e.g., U.S. Pat. Nos. 6,201,980; 6,060,336 and documents cited therein) and have been used in a variety of applications, including as micromotors. In the context of the present invention, therefore, MEMS motors (also known as actuators) can be used to control, for example, rotation of the cutting element. The MEMS motor can be directly fabricated into the device (for example, on one or more wafers on the tip of the catheter) with other required circuit components, to form an integrated, MEMS-driven device. Alternatively, the MEMS can be external to the device, yet connected so as to provide the necessary power. In any event, when used with MEMS-type actuators, the assemblies will further include any fluid channels and/or other transmission devices necessary for MEMS function. Furthermore, including an MEMS micromotor can, in some instances, eliminate the need for, or reduce the length of, the drive shaft. Methods of manufacturing and using suitable MEMS are know to those of skill in the art and include, by way of example, bulk micromachining; surface micromachining; wafer bonding; and LIGA and Electroforming.

The occlusion-removal assembly may also include radio-opaque material, for example as part of the housing, cutting element, or casing. Additionally, radio-opaque bands may be included at the distal tip of the assembly for the purpose of allowing the user to visualize the tip of the assembly in relation to the embolism to be removed. Thus, one or more of the elements (e.g., housing, cutting element, etc.) of the device preferably includes at least one region that is radio-opaque to facilitate visualization in situ.

The device may be deployed using a guide wire, for example the individual components designed to be deployed over a guide wire. In these embodiments, a channel to accommodate the guide wire will be included in one or more of the following elements: housing, cutting element, collection element and balloon.

In certain embodiments, rapid exchange type catheters are used to deploy any of the devices described herein. Rapid exchange catheters are well known to those of skill in the art and are described, for example, in U.S. Pat. Nos. 5,919,164 and 5,827,229. Briefly, rapid exchange typically involves a short guide wire inserted into a slit in the catheter near the proximal end. Partial rapid exchange design can be accomplished using a long guidewire lumen with a slit from the proximal end, extending to several inches (less than 10 cm) from the distal end. The operator can load the device into the catheter over the short rapid exchange length guidewire and insert the assembly into to the coronary arteries.

The device is obviously dimensioned such that is can fit in the selected pathways. For neurovascular indications, the housing may be between 0.1 to 10 mm in diameter; the cutting element between 0.8 and 0.9 mm and the inflated balloon between 1 and 30 mm in diameter. For peripheral vasculature, the dimensions will typically be larger. It will be apparent that such dimensions are not critical to the practice of the invention and be readily determined by the skilled artisan in view of the teachings herein.

Modifications of the procedure and device described above, and the methods of using them in keeping with this invention will be apparent to those having skill in this mechanical and surgical art. These variations are intended to be within the scope of the claims that follow.

What is claimed is:

1. A device for removing occlusions from a vessel, comprising
   a housing element having a distal end, a proximal end and a longitudinal axis, wherein one or more lumens are disposed along the longitudinal axis;
   an embolism collector element;
   a cutting element attached to the distal end of the drive shaft, wherein said cutting element has a surface that is not smooth;
   a casing disposed around the cutting element; and
   an inflatable balloon.

2. The device of claim 1, further comprising a fluid channel in operable communication with the cutting element.

3. The device of claim 1, further comprising a drive shaft disposed along the longitudinal axis of the housing.

4. The device of claim 1, further comprising a power source connected to the cutting element.

5. The device of claim 4, wherein the power source comprises a micro electro mechanical system (MEMS) motor.

6. The device of claim 1, wherein the embolism collector element is disposed along the longitudinal axis of the housing.

7. The device of claim 6, wherein the collector element comprises a vacuum aspirator.

8. The device of claim 1, wherein the cutting element further comprises perforations therein.

9. The device of claim 1, wherein the lumen of the housing which contacts the cutting element is surface-modified.

10. The device of claim 1, wherein the surface of the casing surrounding the cutting element is surface-modified.

11. The device of claim 9 or claim 10, wherein the surface modification comprises braiding or ribbons.

12. The device of claim 1, wherein the casing extends from the distal end of the housing.

13. The device of claim 1, wherein the casing comprises a cage-like structure.

14. The device of claim 1, wherein the inflatable balloon is capable of centering the cutting element.

15. The device of claim 1, wherein the inflatable balloon is capable of at least partially arresting blood flow around the occlusion.

16. A method of removing an occlusion in a vessel, comprising
   accessing a selected site with the device according to claim 1;
   inflating the balloon to the desired dimensions;
   shearing at least a portion of the embolism with the cutting element; and
   removing the sheared fragments of the embolism with the collection element.

17. The method of claim 16, wherein the shearing comprises:
   drawing a portion of the embolism into the housing and manipulating the cutting element to shear the embolism against the interior wall of the housing.

18. The method of claim 16, wherein the device further comprises a casing disposed around the cutting element.

19. The method of claim 18, wherein the shearing comprises extending the cutting element and surrounding casing from the distal end of the housing and manipulating the cutting element against the casing.

* * * * *